(12) United States Patent
Bagwell

(10) Patent No.: US 7,352,111 B2
(45) Date of Patent: Apr. 1, 2008

(54) ELECTROACTIVE POLYMER PUMPING SYSTEM

(75) Inventor: Tony P. Bagwell, Manvel, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 41 days.

(21) Appl. No.: 11/164,699

(22) Filed: Dec. 1, 2005

(65) Prior Publication Data

US 2007/0128059 A1    Jun. 7, 2007

(51) Int. Cl.
*H01L 41/08* (2006.01)
(52) U.S. Cl. .................. 310/328; 310/800; 417/474
(58) Field of Classification Search ................ 310/328, 310/800; 417/474
See application file for complete search history.

(56) References Cited

U.S. PATENT DOCUMENTS

| | | | |
|---|---|---|---|
| 6,294,063 | B1 | 9/2001 | Becker et al. |
| 6,568,470 | B2 | 5/2003 | Goodson, Jr. et al. |
| 6,749,556 | B2 | 6/2004 | Banik |
| 6,781,284 | B1 | 8/2004 | Pelrine et al. |
| 6,812,624 | B1 | 11/2004 | Pei et al. |
| 6,933,659 | B2* | 8/2005 | Krogh et al. ............... 310/330 |
| 2002/0113017 | A1 | 8/2002 | Sheets |
| 2003/0019622 | A1 | 1/2003 | Goodson, Jr. et al. |
| 2003/0117044 | A1 | 6/2003 | Urano et al. |
| 2003/0134426 | A1 | 7/2003 | Jiang et al. |
| 2003/0155012 | A1 | 8/2003 | Smith et al. |
| 2003/0170145 | A1 | 9/2003 | Smith et al. |
| 2003/0192687 | A1 | 10/2003 | Goodson, Jr. et al. |
| 2003/0212306 | A1 | 11/2003 | Banik |
| 2004/0008853 | A1 | 1/2004 | Pelrine et al. |
| 2004/0010180 | A1 | 1/2004 | Scorvo |
| 2004/0068220 | A1* | 4/2004 | Couvillon et al. ......... 604/6.11 |
| 2004/0068224 | A1 | 4/2004 | Couvillon, Jr. et al. |
| 2004/0108479 | A1 | 6/2004 | Garnier et al. |
| 2004/0167375 | A1 | 8/2004 | Couvillon, Jr. |
| 2004/0202603 | A1 | 10/2004 | Fischer et al. |
| 2004/0232807 | A1 | 11/2004 | Pelrine et al. |
| 2004/0234401 | A1* | 11/2004 | Banister ..................... 417/474 |
| 2004/0249236 | A1 | 12/2004 | Hegde et al. |
| 2004/0263028 | A1 | 12/2004 | Pei et al. |
| 2004/0267086 | A1 | 12/2004 | Anstadt et al. |
| 2005/0004425 | A1 | 1/2005 | Banik |
| 2005/0020871 | A1 | 1/2005 | Tozzi et al. |
| 2005/0028522 | A1 | 2/2005 | Fripp et al. |
| 2005/0040733 | A1 | 2/2005 | Goldenberg et al. |
| 2005/0065500 | A1 | 3/2005 | Couvillon, Jr. et al |
| 2005/0089993 | A1 | 4/2005 | Boccazzi et al. |
| 2006/0158065 | A1* | 7/2006 | Pelrine et al. .............. 310/328 |

(Continued)

FOREIGN PATENT DOCUMENTS

EP    1323925 A2    7/2003

(Continued)

*Primary Examiner*—Thomas M. Dougherty
(74) *Attorney, Agent, or Firm*—Winstead PC; Kevin B. McGoff; Bryan P. Galloway

(57) ABSTRACT

An electroactive polymer pump having an electroactive polymer mass forming a channel between an inlet and an outlet and an electrical distribution system in operational connection with the electroactive polymer mass for selectively energizing sections of the electroactive polymer mass to produce an oscillating intrusion of the sections of the EAP mass into the channel to pump a fluid through the channel.

7 Claims, 4 Drawing Sheets

U.S. PATENT DOCUMENTS

| | | | |
|---|---|---|---|
| 2006/0198742 A1* | 9/2006 | DiFoggio et al. | 417/410.1 |
| 2007/0025868 A1* | 2/2007 | Swayze et al. | 417/474 |
| 2007/0029197 A1* | 2/2007 | DiFoggio et al. | 204/450 |

FOREIGN PATENT DOCUMENTS

| | | |
|---|---|---|
| GB | 2359631 A | 8/2001 |
| GB | 2376724 A | 12/2002 |
| GB | 2405256 A | 2/2005 |
| GB | 2405725 A | 3/2005 |
| WO | WO 97/42412 * | 11/1997 |
| WO | 0163094 A1 | 8/2001 |
| WO | 03018955 A1 | 3/2003 |
| WO | 03081762 A1 | 10/2003 |
| WO | 03094800 A2 | 11/2003 |
| WO | 2004031581 A2 | 4/2004 |
| WO | 2004031582 A1 | 4/2004 |
| WO | 2005017301 A2 | 4/2005 |

* cited by examiner

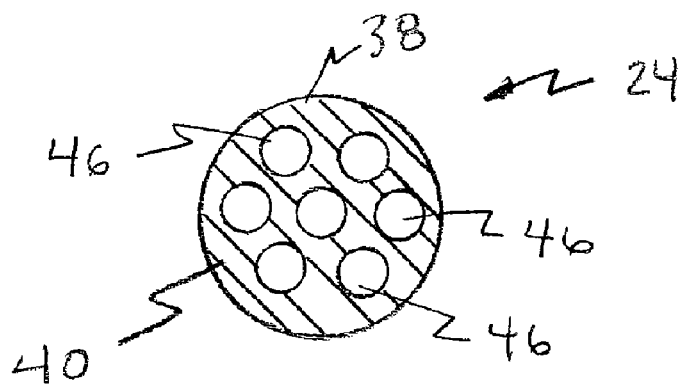
Figure 3
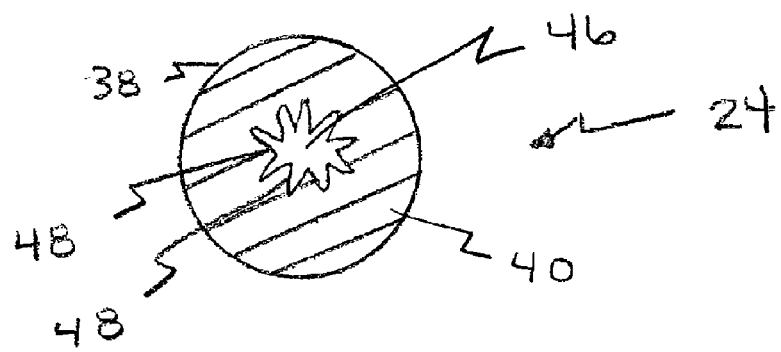
Figure 4
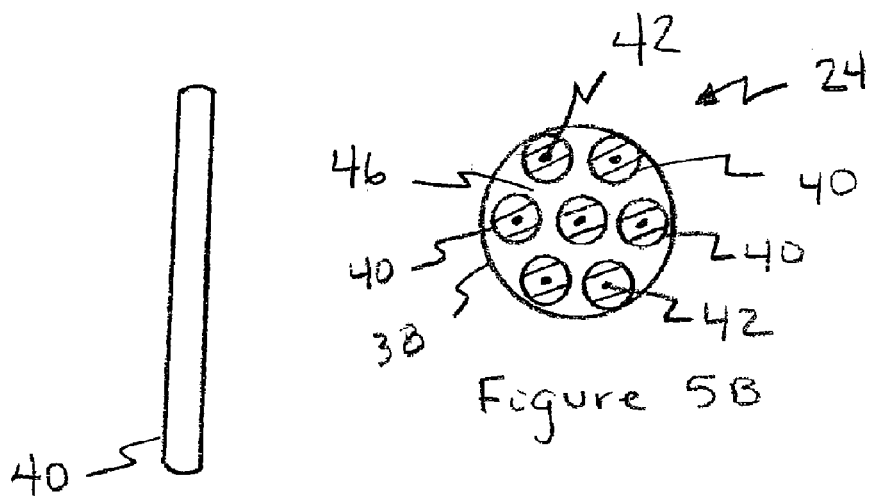
Figure 5A
Figure 5B

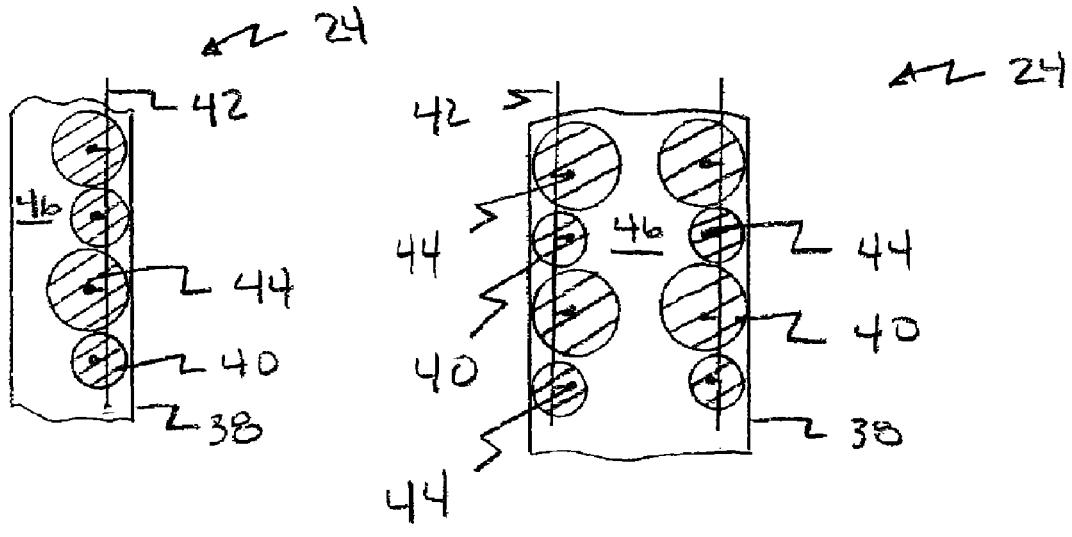
Figure 6
Figure 7
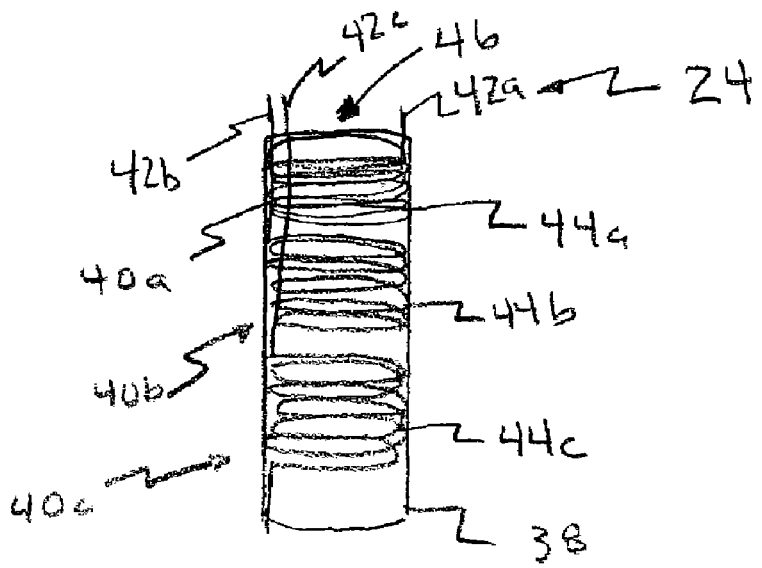
Figure 8

ELECTROACTIVE POLYMER PUMPING SYSTEM

FIELD OF THE INVENTION

The present invention relates in general to pumping systems and more specifically to an electroactive polymer pump for subterranean wells.

BACKGROUND

Submersible pumping systems are well known in the art for lifting liquids such as oil and water and typically comprise a pump and a motor. Traditional mechanical systems are problematic due to their mechanical nature, which is typically complex and contains many individual parts. Mechanical pumping systems often require equipment, such as protectors or seal sections, to service the pumping system. Mechanical pumps exhibit losses of overall efficiency such as motor slippage, pump efficiency, heat generation, mechanical friction, etc. Some mechanical pumps further require extensive shafting to transfer power from the motor on the surface to the downhole pump. The summation of all such mechanical components and systems provides a variety of failure mechanisms that inherently limit the reliability of mechanical pumping systems.

Therefore, there is a desire for a more direct method of transforming electrical energy into fluid displacement for a simpler, more reliable, and more efficient downhole pumping system.

SUMMARY OF THE INVENTION

In the illustrated embodiments the electroactive polymer pump is adapted for use as a submersible pump in a wellbore. However, it should be well understood that the present invention may be utilized in other environments for transporting fluids. The electroactive polymer pumping mechanism provides for a direct transfer of electrical energy to mechanical displacement, thereby eliminating many of the disadvantages of mechanical pumping systems.

The pump relies on an electroactive polymer (EAP) for directly converting electrical power into a dynamical physical motion that lifts fluids. Electroactive polymers are polymers that increase their size when subjected to an electrical current. EAP strands can typically increase their size by a factor of five. This expansion of the volume is the principle by which a pumping action is induced; as the polymer mass expands and increases its volume within a confined spaced, a substantially equal volume of liquid, commensurate with the volumetric dimensional change of the EAP, is mechanically displaced. Embodiments of the present invention may be used for pumping or lifting fluids such as oils, water, mud, slurry, colloids (such as clay and water), or various mixtures and combinations thereof. The EAP pump may be designed and operated for pumping under a wide range of fluid viscosity, pressure, temperature and flow rates, as well as for a wide range of chemical properties of the fluid being pumped, such as acidity, alkalinity, and salt or ionic content.

Accordingly, an embodiment of the electroactive polymer pump includes an electroactive polymer mass forming a channel between an inlet and an outlet and an electrical distribution system in operational connection with the electroactive polymer mass for selectively energizing sections of the electroactive polymer mass. The EAP mass may be positioned within a housing. The housing providing stability to the EAP mass and having an outlet connectable to a production string. The electrical distribution system may include a power source operationally connected to the electrical power source and a controller. The controller facilitates routing electrical energy selectively to sections of the EAP mass to produce an oscillating intrusion of the sections of the EAP mass into the channel to pump a fluid through the channel.

The EAP mass may be constructed in various forms. For example, without limitation the EAP may comprise one or more tubular shaped members, wherein each of the tubular members forms a channel. The EAP mass may comprise fin shaped portions. The EAP mass may comprise a plurality of substantially spherically shaped members. The EAP mass may include a plurality of coiled electroactive polymer strands.

A method of pumping a fluid includes the steps of providing an electroactive polymer pump having an electroactive polymer mass forming a channel between an inlet and an outlet, wherein the electroactive polymer mass has a plurality of sections. Introducing a fluid into the channel and energizing selective sections of the electroactive polymer mass to produce an oscillating intrusion of the sections of the electroactive polymer mass into the channel to pump the fluid through the channel.

The foregoing has outlined the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

The foregoing and other features and aspects of the present invention will be best understood with reference to the following detailed description of a specific embodiment of the invention, when read in conjunction with the accompanying drawings, wherein:

FIG. 3 is a top view of another embodiment of an electroactive polymer pump assembly;

FIG. 4 is a top view of another embodiment of an electroactive polymer pump assembly;

FIG. 5A is a view of a rod shaped electroactive polymer mass;

FIG. 5B is a top view of an embodiment of a electroactive polymer pump assembly utilizing the rod shaped electroactive polymer masses of FIG. 5A;

FIG. 6 is a partial cross-sectional view of another embodiment of the electroactive polymer pump assembly;

FIG. 7 is a partial cross-sectional view of another embodiment of the electroactive polymer pump assembly; and FIG. 8 is a still further embodiment of the electroactive polymer pump assembly.

DETAILED DESCRIPTION

Figure 1:
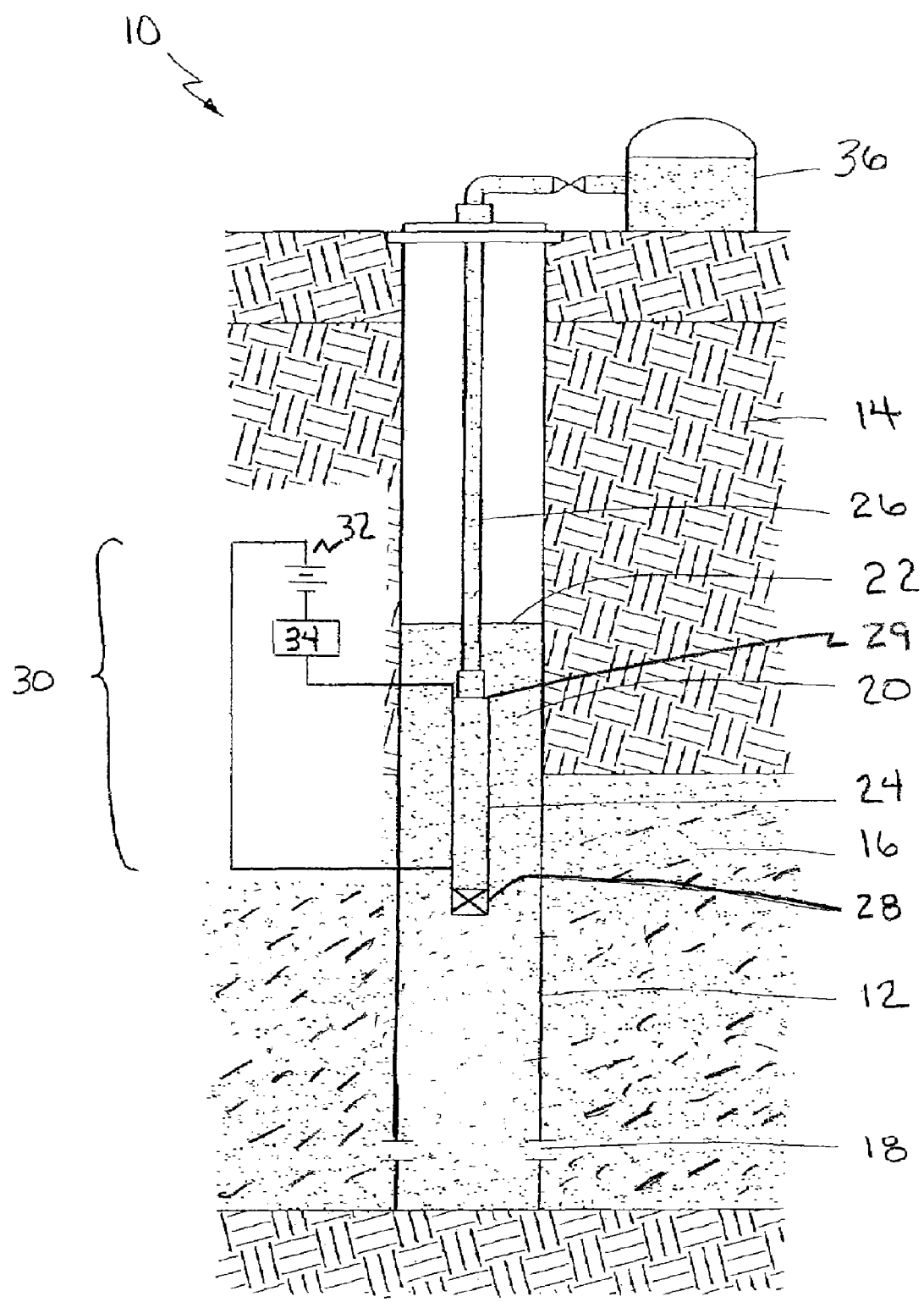
FIG. 1 is a well schematic of an embodiment of an electroactive polymer pump system of the present invention.

Refer now to the drawings wherein depicted elements are not necessarily shown to scale and wherein like or similar elements are designated by the same reference numeral through the several views.

As used herein, the terms "up" and "down"; "upper" and "lower"; and other like terms indicating relative positions to a given point or element are utilized to more clearly describe some elements of the embodiments of the invention. Commonly, these terms relate to a reference point as the surface from which drilling operations are initiated as being the top point and the total depth of the well being the lowest point.

FIG. 1 is a well schematic of an electroactive polymer pumping system of the present invention, generally denoted by the numeral 10. A casing 12 is set in a wellbore formed into the earth 14 and a fluid bearing formation 16. Perforations 18 are formed through casing 12 to facilitate the flow of formation fluid 20 from producing formation 16 into casing 12. Formation fluid 20 collects in the wellbore and has a surface identified at 22.

An electroactive polymer pump assembly 24 is positioned in the wellbore below fluid surface 22 via a production string 26. EAP pump assembly 24 includes a fluid inlet 28 illustrated as a standing valve permitting formation fluid 20 to enter pump assembly 24. Fluid inlet 28 may be located in various positions and may or may not include a valve. An electrical distribution network 30 including an electrical power source 32 and a controller 34 is provided for facilitating the pumping action. Upon actuation, pump assembly 24 pumps formation fluid 20 through production string 26 to a surface facility 36.

Figure 2A:
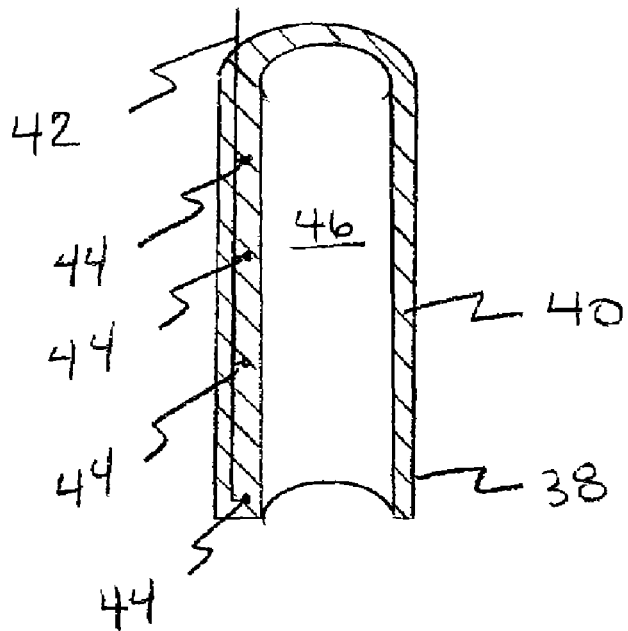
FIG. 2A is a partial cross-sectional view of an electroactive polymer pump assembly of the present invention.

FIG. 2A is a partial cross-sectional view of an EAP pump assembly 24 of the present invention. Pump assembly 24 includes a housing 38, an EAP mass 40 and a conductor 42 having electrodes 44 of electrical distribution system 30 (FIG. 1). FIG. 2A illustrates EAP mass 40 in a static or non-pumping state.

Housing 38 is a tubular member adapted for connection to the production string and provides support for EAP mass 40. As will be better understood in the description of the various embodiments, housing 38 may be comprised of a portion of production string 26 (FIG. 1).

EAP mass 40 in the present embodiment is formed as a substantially cylindrical member forming a channel 46 for transporting fluid 20 (FIG. 1) therethrough. EAP mass 40 may be operationally positioned within housing 38 in various manners. EAP mass 40 may be positioned in housing 38 mechanically or chemically. Examples of positioning means include adhesives and latching mechanisms including lateral notches or grooves formed within housing 38. Heat and/or pressure may be utilized to interconnect housing 38 and EAP mass 40.

EAP mass 40 is operationally connected to electrical distribution system 30 (FIG. 1) via electrical conductor 42. Electrodes 44 are spaced along the length of EAP mass 40 so as to selectively energize sections of EAP mass 40. It should be understood that electrodes 44 may comprise exposed sections of conductor 42 Conductor 42 and terminals 44 are embedded within EAP mass 40 in the embodiment illustrated in FIGS. 2A and 2B.

Figure 2B:
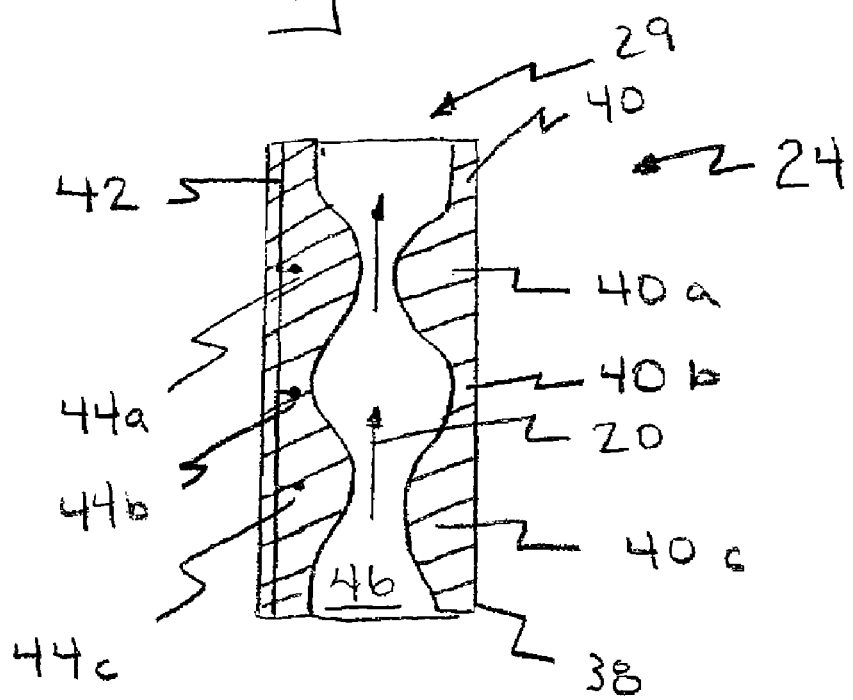
FIG. 2B is a partial cross-sectional view of the pump assembly of FIG. 2A wherein the electroactive polymer mass is in a dynamic or pumping state.

FIG. 2B is a partial cross-sectional view of EAP pump assembly 24 of FIG. 2A wherein EAP mass 40 is in a dynamic or pumping state, transporting fluid 20 through channel 46 from inlet 28 (FIG. 1) through outlet 29.

Operation of pump assembly 24 is further described with reference to FIGS. 1 and 2B. Electrical distribution system 30 includes circuitry or electromechanical components (controller 34) for selectively switching power from power source 32 to electrodes 44 in a systematic or pre-programmed manner, for inducing a desired pumping motion of EAP mass 40. As shown in FIG. 2B illustrating a pumping action, controller 34 routes power to electrode 44c subjecting section 40c of EAP mass 40 to an electric field inducing a transformative alignment of the polymer molecules causing EAP mass section 40c to expand in volume. This may be considered a pseudo-state change from one solid form to another with a lower density, but greater volume. The expansion of section 40c may be controlled in relation to the strength of the electric field that the material is subjected. At the moment that electrode 44c is activated the adjacent electrode 44b may be deactivated or produce a weaker electrical field resulting in EAP mass section 40c expanding to a greater extent than adjacent EAP mass section 40b. Thus as the electric field decreases in relation to the displacement away from activated electrode 44c, the volumetric dimensional expansion of EAP mass 40 may also decrease in some relationship. This effect may also be used in modulating the strength of the electric field, i.e. voltage, switched to an electrode 44 to generate an oscillating response from EAP mass 40. The frequency and phase of the actual mechanical oscillation response to a stimulating electrical waveform may be limited or dampened by electrical and mechanical properties of EAP mass 40, or by the geometry of the particular pump construction.

A positive displacement pumping action may be realized by designing EAP mass 40 so that a section of it completely closes channel 46, preventing any back flow of fluid. In another embodiment, a check valve (not shown) may be connected between sections of EAP pump assembly 24 or EAP mass 40 to prevent back flow. Embodiments of the present invention with positive displacement configurations will be well suited for pumping heavy oils and a wide variety of viscous, high-density fluids. A wear sleeve (not shown) may be inserted between EAP mass 40 and fluid 20 being pumped through channel 46. The wear sleeve may comprise a material chosen to reduce wear or reduce drag, depending on the application and characteristics of the fluid being pumped.

FIG. 3 is a top view of another embodiment of an electroactive pump assembly 24. As shown, EAP mass 40 may include a plurality of channels 46 formed therethrough. Alternatively, each channel 46 may be formed by an individual EAP mass 40 similar to cylindrical EAP mass 40 described in relation to FIGS. 2A and 2B. The separate tubular shaped EAP masses 40 may then be bundled together and positioned within housing 38.

FIG. 4 is a top view of another embodiment of an electroactive pump assembly 24. In this embodiment, EAP mass 40 comprises a plurality of EAP fins 48. Electrical distribution system 30 (FIG. 1) is activated to energize fins 48 to fill channel 46.

FIG. 5A is a view of another embodiment of EAP mass 40. EAP mass 40 is formed as a substantially continuous elongated member. A plurality of elongated or rod shaped EAP masses 40 may be bundled and positioned within housing 38 to provide an EAP pump assembly 24 as shown in FIG. 5B. Channels 46 are formed between the plurality of EAP masses 40. Conductors 42 of electrical distribution system 30 (FIG. 1) are functionally connected to EAP masses 40 to facilitate the pumping action.

FIG. 6 is a partial cross-section view of another embodiment of EAP pump assembly 24. In this embodiment, pump assembly 24 includes a plurality of substantially spherical electroactive active polymer masses interconnected by electrical distribution system 30 of FIG. 1. FIG. 7 illustrates an EAP pump 24 including multiple strings of interconnected substantially spherical EAP masses 40.

FIG. 8 is a still further embodiment of EAP pump assembly 24. In this embodiment EAP mass 40 comprises a plurality of EAP mass sections 40a, 40b, 40c positioned within housing 38 to define a channel 46. The EAP sections will be described with reference to EAP mass section 40a. An electroactive polymer is formed about a wire serving as an electrode connected to conductor 42a and wound into a coil forming EAP section 42a. EAP section 42a is positioned within housing 38 such that a substantially continuous channel 46 is formed by the plurality of EAP sections 40.

From the foregoing detailed description of specific embodiments of the invention, it should be apparent that an electroactive pumping system that is novel has been disclosed. Although specific embodiments of the invention have been disclosed herein in some detail, this has been done solely for the purposes of describing various features and aspects of the invention, and is not intended to be limiting with respect to the scope of the invention. It is contemplated that various substitutions, alterations, and/or modifications, including but not limited to those implementation variations which may have been suggested herein, may be made to the disclosed embodiments without departing from the spirit and scope of the invention as defined by the appended claims which follow.

What is claimed is:

1. A method of pumping a fluid from a wellbore, the method comprising the steps of:

providing a pump comprising an electroactive polymer (EAP) mass forming a channel between an inlet and an outlet, the EAP mass having a plurality of sections;

connecting a production string to the outlet of the pump;

running the pump on the production string into a wellbore;

introducing a fluid into the channel; and selectively energizing the sections of the EAP mass to produce an oscillating intrusion of the sections into the channel to pump the fluid through the channel.

2. The method of claim 1, wherein the electroactive polymer mass comprises a singular tubular shaped member.

3. The method of claim 1, wherein the electroactive polymer mass comprises a plurality of tubular shaped members, each tubular shaped member forming a channel.

4. The method of claim 1, wherein the electroactive polymer mass comprises a plurality of fin shaped portions.

5. The method of claim 1, wherein the electroactive polymer mass comprises a plurality of substantially continuous elongated electroactive polymer members.

6. The method of claim 1, wherein the electroactive polymer mass comprises a plurality of substantially spherically shaped electroactive polymer members.

7. The method of claim 1, wherein each section of the electroactive polymer mass comprises a coiled strand of electroactive polymer.

* * * * *